United States Patent
Klankermayer et al.

(10) Patent No.: US 9,216,933 B2
(45) Date of Patent: Dec. 22, 2015

(54) REDUCTION METHOD FOR THE REDUCTION OF CARBON DIOXIDE AND CARBON DIOXIDE DERIVATIVES

(71) Applicant: RHEINISCH-WESTFÄLISCHE TECHNISCHE HOCHSCHULE AACHEN, Aachen (DE)

(72) Inventors: Jürgen Klankermayer, Essen (DE); Walter Leitner, Aachen (DE); Sebastian Wesselbaum, Aachen (DE); Thorsten Vom Stein, Wermelskirchen (DE)

(73) Assignee: RHEINISCH-WESTFÄLISCHE TECHNISCHE HOCHSCHULE AACHEN (DE)

( * ) Notice: Subject to any disclaimer, the term of this patent is extended or adjusted under 35 U.S.C. 154(b) by 0 days.

(21) Appl. No.: 14/387,362

(22) PCT Filed: Apr. 16, 2013

(86) PCT No.: PCT/EP2013/057942
§ 371 (c)(1),
(2) Date: Sep. 23, 2014

(87) PCT Pub. No.: WO2013/156496
PCT Pub. Date: Oct. 24, 2013

(65) Prior Publication Data
US 2015/0087867 A1    Mar. 26, 2015

(30) Foreign Application Priority Data
Apr. 20, 2012  (EP) .................................... 12165011

(51) Int. Cl.
*C07C 29/153*  (2006.01)
*C07C 29/156*  (2006.01)
*C07C 29/149*  (2006.01)

(52) U.S. Cl.
CPC ............. *C07C 29/153* (2013.01); *C07C 29/149* (2013.01); *C07C 29/156* (2013.01)

(58) Field of Classification Search
CPC .......................... C07C 29/156; C07C 29/153
See application file for complete search history.

(56) References Cited

FOREIGN PATENT DOCUMENTS

WO    WO 2012/052996 A2    4/2012

OTHER PUBLICATIONS

Ekambaram Balaraman et al. "Unprecedented Catalytic Hydrogenation of Urea Derivatives to Amines and Methanol", Angewandte Chemie International Edition, vol. 50, No. 49, Nov. 3, 2011 (200-11-03), pp. 11702-11705.
Ekambaram Balaraman et al. "Direct Hydrogenation of Amides to Alcohols and Amines under Mild Conditions", Journal of the American Chemical Society, vol. 132, No. 47, Dec. 1, 2010, pp. 16756-16758.
Ekambaram Balaraman et al. "Efficient Hydrogenation of organic carbonates, carbamates and formats indicates alternative routes to methanol based on C02 and CO", Nature Chemistry, Nature Publishing Group, GB, vol. 3, No. 8, Jan. 1, 2011, pp. 609-614.
Chelsea A. Huff et al.: "Cascade Catalysis for the Homogeneous Hydrogenation of C02 to Methanol", Journal of the American Chemical Society, vol. 133, No. 45, Oct. 26, 2011, pp. 18122-18125.
Omae et al.: "Aspects of carbon dioxide utilization", Catalysis Today, Elsevier, NL, vol. 115, No. 1-4, Jun. 30, 2006, pp. 33-52.
An English translation of International Search Report issued in connection with International Application No. PCT/EP2013/057942 on Jun. 27, 2013.

*Primary Examiner* — Brian J Davis
(74) *Attorney, Agent, or Firm* — Davidson, Davidson & Kappel LLC

(57) ABSTRACT

A method for the reduction of carbon dioxide and/or carbon dioxide derivatives to methanol comprises the step of hydrogenation carbon dioxide and/or carbon dioxide derivatives in the presence of a Ruthenium-phosphine complex.

8 Claims, No Drawings

REDUCTION METHOD FOR THE REDUCTION OF CARBON DIOXIDE AND CARBON DIOXIDE DERIVATIVES

This application is a U.S. national phase application under 35 U.S.C. of §371 of International Application No. PCT/EP2013/057942, filed on Apr. 16, 2013, which claims priority to EP 12165011.3, filed on Apr. 20, 2012, the disclosures of which are all hereby incorporated by reference herein.

FIELD OF THE INVENTION

The present invention relates to a method for reducing carbon dioxide and carbon dioxide derivatives to methanol.

BACKGROUND OF THE INVENTION

The increasing global energy consumption based on fossil resources and the entailed production of greenhouse gases demands for new strategies of carbon management. Additionally, the depletion of the world-wide oil, gas and coal reserves stresses the need for alternative carbon sources for the production of fuels and chemicals. In this context, the sustainable use of carbon dioxide as carbon resource has been envisaged by chemists and chemical engineers for decades, and the field has seen a highly dynamic development recently. Particularly the effective hydrogenation of carbon dioxide to methanol could contribute strongly to the development of a low-carbon economy, where methanol serves as energy vector and offers a versatile entry into the chemical supply chain.

Therefore there is a constant need in the art for alternative reduction methods of carbon dioxide and carbon dioxide derivatives to methanol, especially methods which are capable of reducing carbon dioxide to methanol directly.

SUMMARY OF THE INVENTION

This object is achieved in the present invention by a method for the reduction of carbon dioxide and/or carbon dioxide derivatives to methanol, comprising the step of:

a) hydrogenating carbon dioxide and/or a carbon dioxide derivative in the presence of a Ruthenium-Phosphine-complex The term "hydrogenation" in the sense of the present invention especially means and/or includes the reaction of the carbon dioxide and/or carbon dioxide derivative with molecular hydrogen and/or a source of molecular hydrogen.

The term "carbon dioxide derivative" especially means and/or includes carbamates, ureas, urethanes and formic acid and its derivatives such as formic acid amides and esters. It should be noted that usually formic acid is not considered a carbon dioxide derivative, however in the context of this invention, formic acid is defined as being a carbon dioxide derivative.

The term "phosphine" in the sense of the present invention especially means and/or includes trivalent phosphororganic compounds, especially compounds with the general formula $PR^1R^2R^3$, $R^1$ to $R^3$ being independent from each other an organic residue such as e.g. a substituted or unsubstituted alkyl, aryl and/or heteroaryl.

The term "Ruthenium-Phosphine-complex" especially means and/or includes a ruthenium complex where in the coordination sphere of the ruthenium a trivalent phosphororganic component is present so that a bond (may it be a covalent and/or a coordination bond) between the ruthenium and the trivalent phosphororganic component is formed at least temporarily during the reaction.

Surprisingly it has been found that by doing so it is possible to reduce carbon dioxide and/or carbon dioxide derivatives to methanol. In case of carbon dioxide it is to the best knowledge of the inventors the first time that a direct reduction to methanol was achieved by a catalytic hydrogenation reaction using an organometallic catalyst. For most applications within the present invention, at least one of the following advantages could be observed:

The reaction can be performed without the need of sophisticated equipment

The reaction can be used on an industrial scale as well as on a small scale

The reaction is be easily adaptable to various applications and their demands

It should be noted that the Ruthenium-Phosphine-complex may be used as a homogenous catalyst or in immobilized form. Also two-phase systems and phase-transfer-catalysis may be used depending on the actual application of the invention. Besides a reaction in batch mode, also a continuous reaction system is possible.

It should furthermore be noted that the Ruthenium-Phosphine-complex may include other ligands such as (but not limited to) carbene, nitrogen containing-ligands such as amines or amides, phosphites, phosphoramidites, phosphoric ethers or esters etc.

According to a preferred embodiment of the present invention, step a) is performed under acidic conditions. This has been shown to greatly increase the efficiency for most applications within the present invention.

The term "acidic conditions" in the sense of the present invention especially means and/or includes that during the reaction at least temporarily more acid than base is present.

According to a preferred embodiment the Phosphine in the Ruthenium-Phosphine-Complex is a Tri(hetero)aryl and/or Bi(hetero)arylalkyl-Phosphine. These compounds have proven themselves in practice.

Generic group definition: Throughout the description and claims generic groups have been used, for example alkyl, alkoxy, aryl. Unless otherwise specified the following are preferred groups that may be applied to generic groups found within compounds disclosed herein:

alkyl: linear and branched C1-C8-alkyl, alkenyl: C2-C6-alkenyl, cycloalkyl: C3-C8-cycloalkyl, alkoxy: C1-C6-alkoxy, alkylene: selected from the group consisting of: methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; cyclohexane-1,1-diyl; cyclohexan-1,2-diyl; cyclohexan-1,3-diyl; cyclohexan-1,4-diyl; cyclopentane-1,1-diyl; cyclopentan-1,2-diyl; and cyclopentan-1,3-diyl, aryl: selected from homoaromatic compounds having a molecular weight under 300, arylene: selected from the group consisting of: 1,2-phenylene; 1,3-phenylene; 1,4-phenylene; 1,2-naphtalenylene; 1,3-naphtalenylene; 1,4-naphtalenylene; 2,3-naphtalenylene; 1-hydroxy-2,3-phenylene; 1-hydroxy-2,4-phenylene; 1-hydroxy-2,5-phenylene; and 1-hydroxy-2,6-phenylene, heteroaryl: selected from the group consisting of: pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and isoindolyl, wherein the heteroaryl may be connected to the compound via any atom in the ring of the selected heteroaryl, Unless otherwise specified the following are more preferred group restrictions that may be applied to groups found within compounds disclosed herein:
alkyl: linear and branched C1-C6-alkyl,
alkenyl: C3-C6-alkenyl,
cycloalkyl: C6-C8-cycloalkyl,
alkoxy: C1-C4-alkoxy,
alkylene: selected from the group consisting of: methylene; 1,2-ethylene; 1,3-propylene; butan-2-ol-1,4-diyl; 1,4-butylene; cyclohexane-1,1-diyl; cyclohexan-1,2-diyl; cyclohexan-1,4-diyl; cyclopentane-1,1-diyl; and cyclopentan-1,2-diyl,
aryl: selected from group consisting of: phenyl; biphenyl; naphthalenyl; anthracenyl; and phenanthrenyl,
arylene: selected from the group consisting of: 1,2-phenylene; 1,3-phenylene; 1,4-phenylene; 1,2-naphtalenylene; 1,4-naphtalenylene; 2,3-naphtalenylene and 1-hydroxy-2,6-phenylene,
heteroaryl: selected from the group consisting of: pyridinyl; pyrimidinyl; quinolinyl; pyrazolyl; triazolyl; isoquinolinyl; imidazolyl; and oxazolidinyl, wherein the heteroaryl may be connected to the compound via any atom in the ring of the selected heteroaryl, heteroarylene: selected from the group consisting of: pyridin 2,3-diyl; pyridin-2,4-diyl; pyridin-2,6-diyl; pyridin-3,5-diyl; quinolin-2,3-diyl; quinolin-2,4-diyl; isoquinolin-1,3-diyl; isoquinolin-1,4-diyl; pyrazol-3,5-diyl; and imidazole-2,4-diyl.

According to a preferred embodiment of the present invention, the Ruthenium-Phosphine-Complex comprises more than one Phosphine, i.e. that in the coordination sphere of the ruthenium two or more trivalent phosphororganic components are present so that bonds (may it be covalent or coordination bonds) between the ruthenium and the phosphororganic components are formed at least temporarily during the reaction. Especially preferred are Ruthenium-Triphosphine-Complexes.

It should be noted that the present invention is not limited to Ruthenium-Phosphine-Complexes where all phosphines are bound to the Ruthenium. Actually in many applications of the present invention, the phosphine is used in excess so that also non-bound phosphines are present.

According to a preferred embodiment of the present invention, the Ruthenium-Phosphine-Complex comprises a bisphosphororganic component, trisphosphororganic component or a higher phosphororganic component. The term "bisphosphororganic component" and "trisphosphororganic component" in this context especially means and/or includes organic components in which two and three, respectively, trivalent phosphors are present. It should be noted that not necessarily all of the phosphines are bound to the Ruthenium during step a). Especially if higher phosphororganic components (in the sense of the present invention organic compounds with more than three trivalent phosphors) are used, not all of the phosphors are catalytically involved in the reaction; nevertheless these compounds are preferred compounds within the present invention as well.

Especially preferred in this context are phosphororganic components where the "bridging" moiety between the phosphors is an alkyl or alkylene moiety whereas the further ligands at the phosphor are aryl or heteroaryl. An especially preferred component in this context is Triphos=1,1,1-tris (diphenylphosphinomethyl)ethane, which has the following structure:

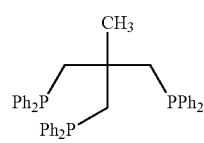

According to a preferred embodiment of the present invention, the Ruthenium-Phosphine-Complex comprises a bisphosphororganic component, trisphosphororganic component or a higher phosphororganic component which furthermore includes one or more donor moieties which can serve as ligands for the Ruthenium. Especially preferred in this context are carbenes, nitrogen containing-ligands such as amines or amides, phosphites, phosphoramidites, phosphoric ethers or esters. These compounds have proven themselves in practice. Yet especially preferred are bisphosphororganic components with one further donor moeity.

It should be noticed that according to one preferred embodiment of the present invention, the Ruthenium-Phosphine-complex may (prior to the reaction) comprise one or more "volatile" or easy removable ligand which stabilizes the complex so that it may be handled before the reaction but during the reaction sequence is replaced by the reactants. Suitable ligands are i.e. trimethylmethane, cyclopentadienyl, allyl, methylallyl, ethylene, cyclooctadiene, acetylactonate, acetate or carbon monoxide.

According to a preferred embodiment of the present invention, step a) is performed under acidic conditions whereby the (initial) concentration of acid is $\geq 0.5$ to $\leq 20$ times the concentration of Ruthenium (in mol:mol). It has been found that by doing so the reaction speed and the TON can be increased for many applications within the present invention. More preferred the concentration of acid is $\geq 0.8$ to $\leq 10$ times the concentration of Ruthenium (in mol:mol), yet more preferred $\geq 1$ to $\leq 2$ times.

According to a preferred embodiment of the present invention, step a) is performed under acidic conditions whereby the acid is selected out of the group comprising organic or inorganic acids, especially sulfonic acids, especially methanesulfonic acid, trifluormethansulfonic acid, p-toluolsulfonic acid, p-bromobenzosulfonic acid, p-nitrobenzosulfonic acid, sulfuric acid, hydrochloric acid, hydrofluoric acid, trifluoracetic acid, perchloric acid or mixtures thereof. Even more preferred are acids which provide weak coordinating anions after deprotonation, such as bis(trifluoromethane)sulfonimide or mixtures thereof with aforementioned acids. These compounds have proven themselves in practice.

According to a preferred embodiment of the present invention, step a) is carried out at a temperature of $\geq 0°$ C. to $\leq 200°$ C., preferably $\geq 20°$ C. to $\leq 190°$ C., more preferred $\geq 60°$ C. to $\leq 180°$ C., even more preferred $\geq 100°$ C. to $\leq 170°$ C. and most preferred at $\geq 120°$ C. to $\leq 160°$ C. This has been shown to be most efficient for most applications within the present invention, According to a preferred embodiment of the present invention, step a) is carried out in a dipolar protic or aprotic solvent or in $CO_2$. Preferred solvents are ethers (also cyclic ethers such as THF), alcohols, preferably ethanol or methanol and $CO_2$ (either liquid or near or supercritical). $CO_2$ is insofar a preferred solvent since it is also one of the possible educts.

According to a preferred embodiment of the present invention, step a) is carried out in the presence of an alcohol, especially ethanol and/or methanol. It has been shown for many applications that this speeds up the reaction.

According to a preferred embodiment of the present invention, step a) is carried out at an initial hydrogen pressure of ≥1 bar, preferably ≥10 bar and most preferred ≥20 bar. This has been shown to greatly increase the reaction speed and efficiency for most applications of the present invention.

In case $CO_2$ is a reactand, it is especially preferred that step a) is carried out at an initial $CO_2$ pressure of ≥1 bar, preferably ≥5 bar and most preferred ≥10 bar. This has been shown to greatly increase the reaction speed and efficiency for most applications of the present invention, too.

According to a preferred embodiment of the present invention, the method furthermore comprises a step a0) to be performed before step a):

a0) Reacting suitable precursor compounds to form the Ruthenium-Phosphine-Complex Suitable Ruthenium-containing precursor compounds include $Ru(acac)_3$, $[Ru(cod)(methylallyl)_2]$ $Ru(nbd)(methylallyl)_2$, $Ru(ethylene)2(methylallyl)_2$.

Step a0) may be carried out at room temperature or at the same temperature at step a).

The aforementioned components, as well as the claimed components and the components to be used in accordance with the invention in the described embodiments, are not subject to any special exceptions with respect to their size, shape, material selection and technical concept such that the selection criteria known in the pertinent field can be applied without limitations.

Additional details, characteristics and advantages of the object of the invention are disclosed in the subclaims and the following description of the respective Examples which are for illustration of the invention only and non-binding.

DETAILED DESCRIPTION OF THE INVENTION

Examples

In the following, the following catalyst systems are used, being referred to as complex 1 and 2.

Complex 1 is a Ruthenium-phosphine-catalyst which is formed in situ out of $Ru(acac)_3$ and Triphos (whose structure has been described above).

Hydrogenations using the Complex 1 were carried out according to the following General Procedures:
General Procedure for Formate Ester Hydrogenation Experiments All high pressure batch experiments were conducted in stainless steel autoclaves (inner volume=13 mL) equipped with a glass inlet and a magnetic stir bar. Prior to use, the autoclave was dried at 60° C. in high vacuum and repeatedly filled with argon. Under an argon atmosphere, $Ru(acac)_3$ (0.025 mmol), Triphos (0.05 mmol), ethyl formate (2.5 mmol), 1.0 mL THF and 1.0 mL of a solution of methane sulfonic acid in THF (3.7 mg/mL) were weighed into a Schlenk tube. The reaction solution was transferred to the autoclave via cannula. The autoclave was pressurized with $H_2$ to 30 bar and the mixture stirred and heated at 140° C. in an oil bath. After 24 h, the autoclave was cooled to ca. 0° C. in an ice bath and then carefully vented. The reaction solution was analyzed by $^1$H-NMR with internal standard mesitylene.
General Procedure for $CO_2$ Hydrogenation Experiments All high pressure batch experiments were conducted in stainless steel autoclaves (inner volume=13 mL) equipped with a glass inlet and a magnetic stir bar. Prior to use, the autoclave was dried at 60° C. in high vacuum and repeatedly filled with argon. Under an argon atmosphere, $Ru(acac)_3$ (0.025 mmol), triphos (0.05 mmol), ethanol (10 mmol), 0.5 mL THF and 1.0 mL of a solution of methane sulfonic acid in THF (3.7 mg/mL) were weighed into a Schlenk tube. The reaction solution was transferred to the autoclave via cannula. The autoclave was pressurized with $CO_2$ to 10 bar and then $H_2$ was added up to a total pressure of 40 bar. The reaction mixture was stirred and heated to 140° C. in an oil bath. After 24 h, the autoclave was cooled to ca. 0° C. in an ice bath and then carefully vented. The reaction solution was analyzed by $^1$H-NMR with internal standard mesitylene and the results confirmed by gas chromatography using heptane as internal standard.

Complex 2 refers to [(Triphos)Ru(TMM)] (TMM=Trimethylenemethane) which was made the following way:

A 35 mL schlenk tube was charged with 159.5 mg (0.5 mmol) $[Ru(cod)(methylallyl)_2]$ and 312.0 mg 1,1,1-tris (diphenylphosphinomethyl)ethane (Triphos) in 25 mL toluene. After heating for 2 h at 110° C., the resulting solution was concentrated in vacuo and treated with 10 mL of pentane. The precipitating complex was isolated and washed 3 times with 10 mL pentane. After drying, complex 2 was obtained as a bright yellow powder in 76% yield.

$^1$H-NMR (600 MHz, $d^2$-dichloromethane): δ 7.16-7.07 (m, 18H, $C_{Ar}$—H), 6.99 (m, 12H, $C_{Ar}$—H), 2.28 (bs, 6H, P—$CH_2$), 1.67 (bs, 6H, C—$CH_2$), 1.44 (s, 3H, $CH_3$).

$^{13}$C-NMR (125 MHz, $d^2$-dichloromethane): δ 141.0 (m, $C_{Ar}$), 132.2 (m, $C_{Ar}$—H), 127.6 (s, $C_{Ar}$—H), 127.3 (s, $C_{Ar}$—H), 106.5 (bs, $C(CH_2)_3^{2-}$), 43.2 (m, $C(CH_2)_3^{2-}$), 38.9 (q, $J_{C-P}$=9.7 Hz, $CH_3$), 38.2 (m, $(Ph_2PCH_2)_3C$—$CH_3$), 35.6 (m, P—$CH_2$) ppm.

$^{31}$P-NMR (243 MHz, $d^8$-toluene): δ 34.4 (s, 3P) ppm.

HR-MS (EI) $C_{41}H_{45}P_3Ru$: Calc.: 780.177 m/z. Found: 780.178 m/z.

Hydrogenations using Complex 2 were carried out in analogy mutatis mutandis to the above-described General procedures for Complex 1, only that the complex 2 was used in pure form (0.025 mmol). In the following table I, the results for hydrogenation of formate esters are given.

In the table, "MSA" stands for methanesulfonic acid (1.5 eq. to Ruthenium in mol/mol in all experiments, wherever present). "R" is the ester residue of the formate ester, i.e. either methyl or ethyl esters were used. "TON" is the turnover-number (in mol MeOH/mol catalyst).

TABLE I

| Entry | Complex. | Acid | R | pH$_2$ [bar] | TON |
|---|---|---|---|---|---|
| 1 | 1 | MSA | Et | 50 | 75 |
| 2 | 1 | MSA | Me | 50 | 74 |
| 3 | 2 | — | Et | 30 | 5 |
| 4 | 2 | MSA | Et | 30 | 77 |

It can be seen that the inventive method is a clean and efficient reduction method for formate esters. The presence of acid (although not necessarily needed) greatly increases the reaction efficiency.

In the following table II, the results for hydrogenation of $CO_2$ is given.

TABLE II

| Entry | Complex | Acid | Additive | pH$_2$ [bar] | pCO$_2$ [bar] | TON |
|---|---|---|---|---|---|---|
| 1 | 1 | — | EtOH | 30 | 10 | 2 |
| 2 | 1 | MSA | EtOH | 30 | 10 | 52 |
| 3 | 2 | — | EtOH | 30 | 10 | 8 |
| 4 | 2 | MSA | EtOH | 30 | 10 | 63 |

TABLE II-continued

| Entry | Complex | Acid | Additive | pH$_2$ [bar] | pCO$_2$ [bar] | TON |
|---|---|---|---|---|---|---|
| 5 | — | MSA | EtOH | 30 | 10 | 0 |
| 6 | 1 | MSA | EtOH | 30 | — | 0 |
| 7 | 1 | MSA | d$_4$-MeOH | 30 | 10 | 24 |

In the table, "MSA" stands for methanesulfonic acid (1.5 eq. to Ruthenium in mol/mol in all experiments wherever present), "TON" is the turnover-number (in mol MeOH/mol catalyst). "Additive" means that 10 mmol of Ethanol (or d$_4$-MeOH in Entry 7) were added.

In Table II, the clear reduction of CO$_2$ in a single reaction to MeOH can be observed. Furthermore, series of control experiments confirmed the origin of the observed methanol from the inventive Ru-catalysed CO$_2$ hydrogenation process. No methanol was formed in the absence of CO$_2$ (entry 6). Also the presence of acid alone did not lead to any detectably formation of CO$_2$ reduction products as expected (entry 5). Most significantly, the formation of methanol from CO$_2$ was also unambiguously proven using deuterium labelled MeOH as alcohol component (entry 7). The incorporation of hydrogen from the gaseous reagents was clearly evident in the NMR spectroscopic analysis of the methanol in the reaction mixture.

Additional hydrogenation results are shown in Table III:

| Entry | Complex | Acid (eq.) | Time [h] | pH$_2$ [bar] | pCO$_2$ [bar] | TON |
|---|---|---|---|---|---|---|
| 1 | 1 | MSA (1.0) | 24 | 30 | 10 | 39 |
| 2 | 1 | MSA (3.0) | 24 | 30 | 10 | 30 |
| 3 | 1 | MSA (5.0) | 24 | 30 | 10 | 25 |
| 4 | 1 | p-TsOH (1.5) | 24 | 30 | 10 | 43 |
| 5 | 1 | MSA (1.5) | 8 | 30 | 10 | 19 |
| 6 | 1 | MSA (1.5) | 72 | 30 | 10 | 65 |
| 7 | 1 | MSA (1.5) | 24 | 30 | 10 | 46 |
| 8 | 1 | MSA (1.5) | 24 | 60 | 20 | 135 |
| 9 | 2 | HNTf$_2$ (1.0) | 24 | 30 | 10 | 86 |
| 10 | 2 | HNTf$_2$ (1.5) | 24 | 30 | 10 | 77 |
| 11 | 2 | HNTf$_2$ (3.0) | 24 | 30 | 10 | 65 |
| 12 | 2 | HNTf$_2$ (1.0) | 24 | 60 | 20 | 221 |
| 13 | 2 | HNTf$_2$ (1.0) | 24 | 60 | 20 | 310 |

In the table, "MSA" stands for methanesulfonic acid, "p-TsOH" for p-toluenesulfonic acid, "HNTf$_2$" for bis(trifluoromethane)sulfonamide. "TON" is the turnover-number (in mol MeOH/mol catalyst). 10 mol EtOH, (in Entry 7, 20 mmol) EtOH were added. In Entry 13, approx. the half amount of catalyst 2 was used (0.013 mmol) as in the General Formula.

In Table III it can be seen that the TON increased from 19 after 8 h over 52 after 24 h to 65 after 72 h, demonstrating a significant catalytic activity even after prolonged reaction times (entry 5-6). Most significantly, raising the carbon dioxide pressure to 20 bar and the hydrogen pressure to 60 bar increased the TON to 135 (entry 8). Even more significantly the activity could be improved by using complex 2 together with bis(trifluoromethane)sulfonamide (HNTf$_2$) as acidic additive (entries 9-13). Using 1 equivalent of HNTf$_2$ gave the best result (entries 9-11). Raising the carbon dioxide pressure to 20 bar and the hydrogen pressure to 60 bar again resulted in an increase in TON to 221. With halved catalyst concentration, an even higher TON of 310 was achieved.

Table IV shows additional results of the hydrogenation of CO$_2$ to methanol in the absence of alcohol additives. Reaction conditions were: Complex: 25.0 µmol (unless otherwise stated), 2.08 mL Solvent, 20 bar CO$_2$+60 bar H$_2$ (at room temperature), 140° C., 24 h;

TABLE IV

| Entry | Complex | Acid(eq.) | Solvent | TON |
|---|---|---|---|---|
| 1 | 2 | HNTf$_2$ (1.0) | THF | 228 |
| 2 | 2 | HNTf$_2$ (1.5) | THF | 196 |
| 3 | 2 | HNTf$_2$ (2.0) | THF | 181 |
| 4 | 2 | p-TsOH (1.0) | THF | 112 |
| 5 | 2 | p-TsOH (1.5) | THF | 134 |
| 6 | 2 | p-TsOH (2.0) | THF | 102 |
| 7 | 2 (12.5 µmol) | HNTf$_2$ (1.0) | THF | 335 |
| 8 | 2 (6.3 µmol) | HNTf$_2$ (1.0) | THF | 442 |
| 9 | 2 | HNTf$_2$ (1.0) | Methyltetrahydrofurane | 156 |
| 10 | 2 | HNTf$_2$ (1.0) | dioxane | 194 |

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. The invention's scope is defined in the following claims and the equivalents thereto. Furthermore, reference signs used in the description and claims do not limit the scope of the invention as claimed.

The invention claimed is:

1. A method for the reduction of carbon dioxide and/or carbon dioxide derivatives and/or formic acid and/or formic acid amides and/or formic acid esters to methanol, comprising the step of:
   a) hydrogenating carbon dioxide and/or a carbon dioxide derivative and/or formic acid and/or formic acid amides and/or formic acid esters in the presence of a Ruthenium-Phosphine-Complex
   wherein the carbon dioxide derivative are selected from the group consisting of carbamates, ureas, and urethanes and wherein the Ruthenium-Phosphine-Complex includes a phosphine selected from the group consisting of a bisphosphororganic component, a trisphosphororganic component or a higher phosphororganic component.

2. The method according to claim 1, wherein step a) is performed under acidic conditions.

3. The method according to claim 1, wherein the Phosphine in the Ruthenium-Phosphine-Complex is a Tris(hetero)aryl and/or Bis(hetero)arylalkyl Phosphine.

4. The method according to claim 1, wherein step a) is performed under acidic conditions whereby the initial concentration of acid is >0.5 to <20 times the concentration of Ruthenium (in mol:mol).

5. The method according to claim 4, wherein step a) is performed under acidic conditions whereby the acid is selected from the group consisting of sulfonic acids.

6. The method according to claim 1, wherein step a) is carried out at an initial hydrogen pressure of >1 bar.

7. The method according to claim 1, wherein step a) is carried out in a dipolar protic or aprotic solvent or in $CO_2$.

8. The method according to claim 4, wherein step a) is performed under acidic conditions wherein the acid is selected from the group consisting of methanesulfonic acid, trifluormethansulfonic acid, p-toluolsulfonic acid, p-bromobenzosulfonic acid, p-nitrobenzosulfonic acid, sulfuric acid, hydrochloric acid, hydrofluoric acid, trifluoracetic acid, perchloric acid, bis(trifluoromethane)sulfonimide and mixtures thereof.

* * * * *